(12) United States Patent
Ben-Jacob et al.

(10) Patent No.: US 8,594,762 B2
(45) Date of Patent: *Nov. 26, 2013

(54) SYSTEM FOR AND METHOD OF POSITIONING CELLS AND DETERMINING CELLULAR ACTIVITY THEREOF

(75) Inventors: Eshel Ben-Jacob, Tel Aviv (IL); Ronen Segev, Ramat Gan (IL); Itay Baruchi, Tel Aviv (IL); Eyal Hulata, Rishon-LeZion (IL); Yoash Shapira, Petah Tikva (IL); Yael Hanein, Caesarea (IL); Tamir Gabay, Kadima (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 918 days.

This patent is subject to a terminal disclaimer.

(21) Appl. No.: 12/703,241

(22) Filed: Feb. 10, 2010

(65) Prior Publication Data
US 2010/0136605 A1 Jun. 3, 2010

Related U.S. Application Data

(62) Division of application No. 10/534,127, filed as application No. PCT/IL03/00913 on Nov. 3, 2003, now Pat. No. 7,684,844.

(60) Provisional application No. 60/423,973, filed on Nov. 6, 2002.

(51) Int. Cl.
*A61B 5/04* (2006.01)
*A61N 1/05* (2006.01)

(52) U.S. Cl.
USPC ............................ 600/377; 600/378; 607/116

(58) Field of Classification Search
USPC .................................. 600/377, 378; 607/116
See application file for complete search history.

(56) References Cited

U.S. PATENT DOCUMENTS

| 4,461,304 A | 7/1984 | Kuperstein |
| 4,969,468 A | 11/1990 | Byers et al. |

(Continued)

FOREIGN PATENT DOCUMENTS

WO WO 2004/041996 5/2004

OTHER PUBLICATIONS

International Search Report Dated Sep. 14, 2004 From the International Searching Authority Re.: Application No. PCT/IL03/00913.

(Continued)

*Primary Examiner* — Lee S Cohen

(57) ABSTRACT

A device for positioning at least one cell in at least one addressable position, the device comprising a substrate formed with at least one addressable pore and at least one channel embedded in the substrate and being in fluid communication with the at least one pore. The at least one pore and the at least one channel are designed and constructed such that an under-pressure formed in the at least one channel results in vacuum adherence of the at least one cell onto the at least one pore, such that a single cell is vacuum adhered onto a single pore. In one embodiment, the substrate is a non-conductive substrate and is further formed with one or more electrode structures, where each of the electrode structures is positioned in one of the pores. In an additional embodiment the device is designed locatable onto an organ, such as a brain.

25 Claims, 12 Drawing Sheets
(5 of 12 Drawing Sheet(s) Filed in Color)

(side view)

(56) References Cited

U.S. PATENT DOCUMENTS

| | | | |
|---|---|---|---|
| 6,699,697 B2 | 3/2004 | Klemic et al. | |
| 7,684,844 B2 * | 3/2010 | Ben-Jacob et al. | 600/377 |
| 2004/0006264 A1 | 1/2004 | Mojarradi et al. | |
| 2004/0146849 A1 | 7/2004 | Huang et al. | |
| 2006/0129043 A1 | 6/2006 | Ben-Jacob et al. | |

OTHER PUBLICATIONS

Notice of Allowance Dated Nov. 2, 2009 From the US Patent and Trademark Office Re.: U.S. Appl. No. 10/534,127.

Official Action Dated Dec. 3, 2008 From the US Patent and Trademark Office Re.: U.S. Appl. No. 10/534,127.

Official Action Dated May 5, 2009 From the US Patent and Trademark Office Re.: U.S. Appl. No. 10/534,127.

Official Action Dated May 15, 2008 From the US Patent and Trademark Office Re.: U.S. Appl. No. 10/534,127.

Official Action Dated Aug. 25, 2008 From the US Patent and Trademark Office Re.: U.S. Appl. No. 10/534,127.

Canepari et al. "Experimental Analysis of Neural Dynamics in Cultured Cortical Networks and Transitions Between Different Patterns of Activity", Biological Cybernetics, 77: 153-162, 1997.

Egert et al. "A Novel Organotypic Long-Term Culture of the Rat Hippocampus on Substrate-Integrated Multielectrode Arrays", Brain Research Protocols, 2: 229-242, 1998.

Hamill et al. "Improved Patch-Clamp Techniques for High-Resolution Curent Recording From Cells and Cell-Free Membrane Patches", Pflugers Archives, 391(2): 85-100, 1981. Abstract.

Heuschkel et al. "Buried Microchannels in Photopolymer for Delivering of Solutions to Neurons in a Network", Sensors and Actuators B, 48: 356-361, 1998.

Huang et al. "Growth of Highly Oriented Carbon Nanotubes by Plasma-Enhanced Hot Filament Chemical Vapor Deposition", Applied Physics Letters, 73(26): 3845-3847, 1998.

Jimbo et al. "Simultaneous Measurement of Intracellular Calcium and Electrical Activity From Patterned Neural Networks in Culture", IEEE Transactions on Biomedical Engineering, 40(8): 804-810, 1993.

Kim et al. "Interfacing Silicon Nanowires With Mammalian Cells", Journal of the American Chemical Society, JACS, 129(23): 7228-7229, Mar. 1, 2007.

Maiti et al. "Measuring Serotonin Distribution in Live Cells With Three-Photon Excitation", Science, 275: 530-532, 1997.

Markram et al. "Redistribution of Synaptic Efficacy Between Neocortical Pyramidal Neurons", Nature, 382: 807-810, 1996.

Ren et al. "Growth of a Single Freestanding Multiwall Carbon Nanotube on Each Nanonickel Dot", Applied Physics Letters, 75(8): 1086-1088, 1999.

Ren et al. "Large Arrays of Well-Aligned Carbon Nanotubes", Proceedings of 13th International Winter School on Electronic Properties of Novel Materials, Kirchberg/Tirol, AT, p. 263-267, Feb. 27-Mar. 6, 1999.

Ren et al. "Synthesis of Large Arrays of Well-Aligned Carbon Nanotubes on Glass", Science, 282: 1105-1107, 1998.

Segev et al. "Long Term Behavior of Lithographically Prepared In Vitro Neuronal Networks", Physical Review Letters, 88(11): 118102-1-118102-4, 2002.

Wheeler et al. "Multi-Neuron Patterning and Recording", Enabling Technologies for Cultured Neuronal Networks, Academic Press, 20 P. 1994.

\* cited by examiner

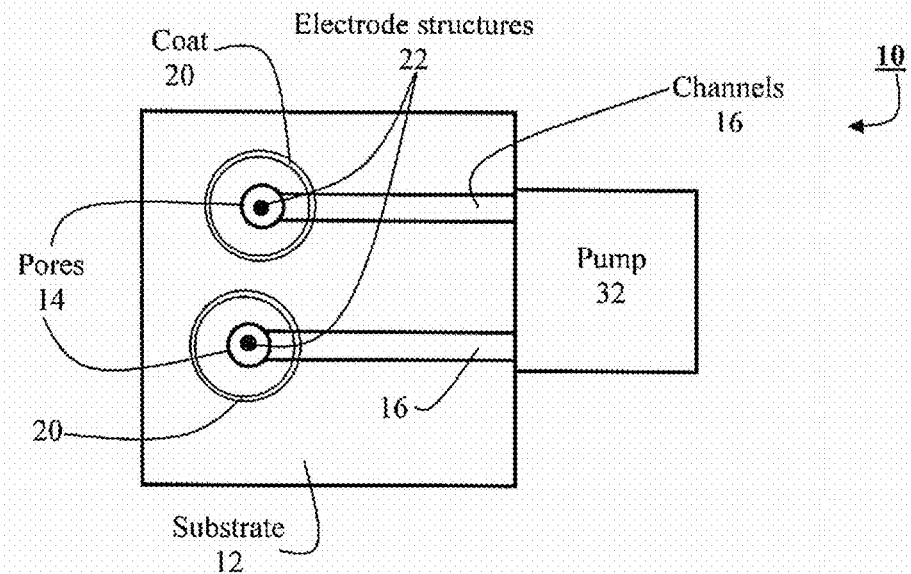
Fig. 1a (top view)
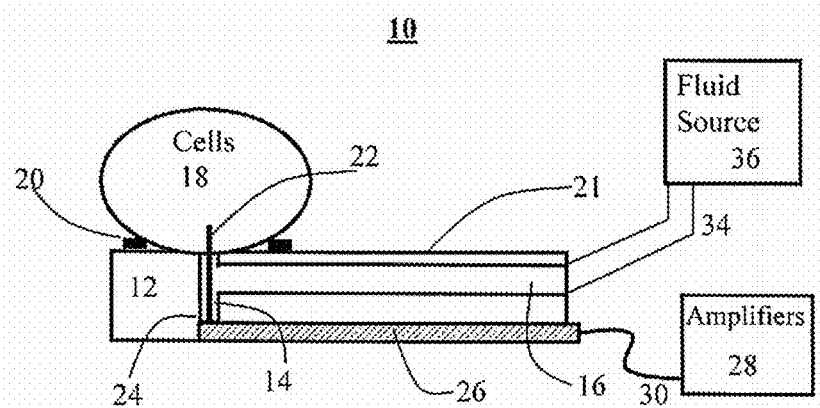
Fig. 1b (side view)

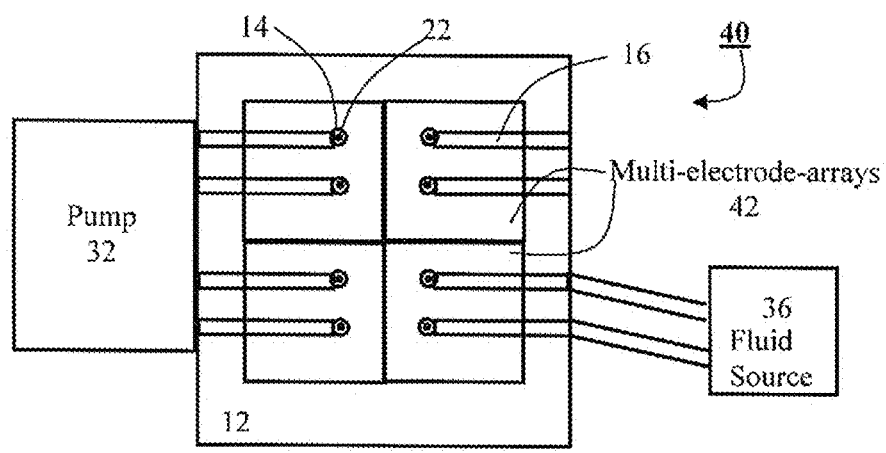
Fig. 2
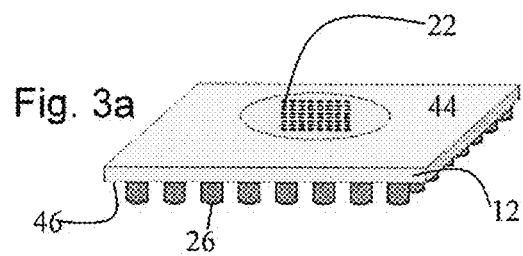
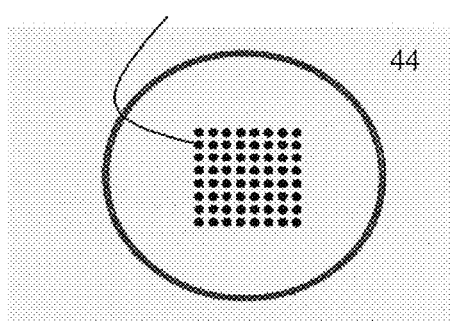
Fig. 3b (top view)
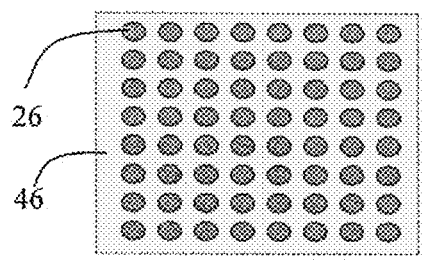
Fig. 3c (bottom view)

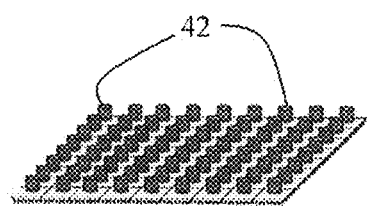 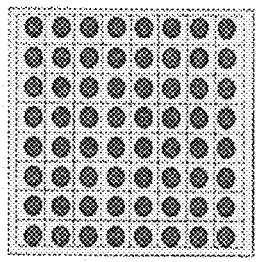 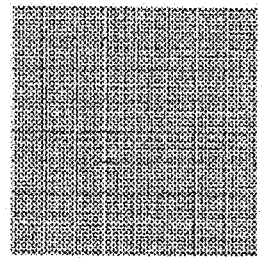
Fig. 4a  Fig. 4b (top view)  Fig. 4c (bottom view)

Fig. 12a
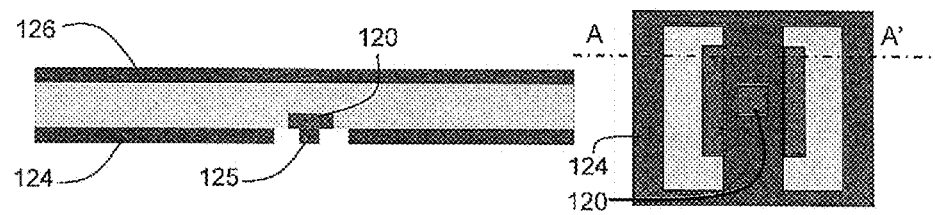
Fig. 12c
Fig. 12b
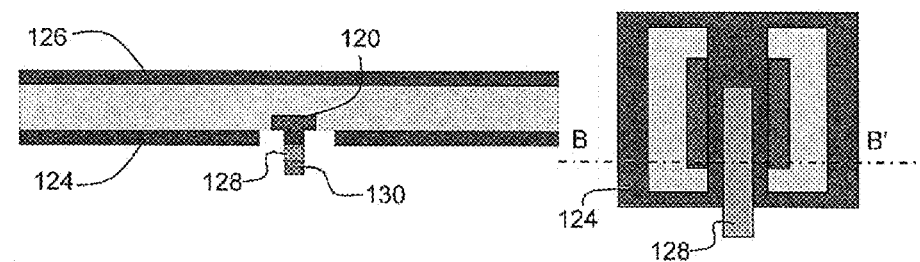
Fig. 12e
Fig. 12d
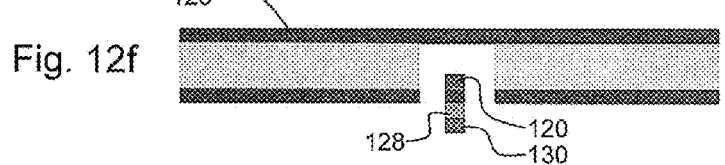
Fig. 12f
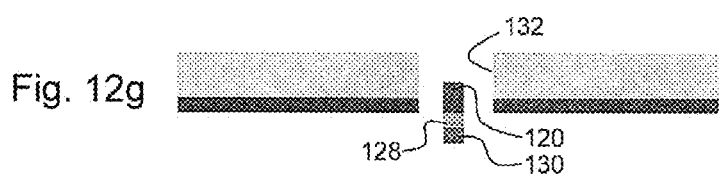
Fig. 12g
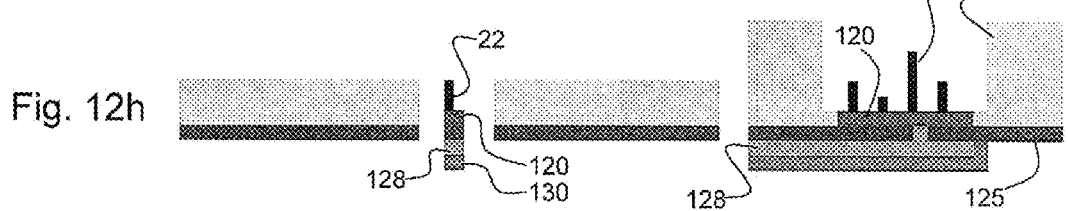
Fig. 12h
Fig. 12i

SYSTEM FOR AND METHOD OF POSITIONING CELLS AND DETERMINING CELLULAR ACTIVITY THEREOF

RELATED APPLICATIONS

This application is a Division of U.S. patent application Ser. No. 10/534,127 filed on Nov. 18, 2005, now U.S. Pat. No. 7,684,844, which is a National Phase of PCT Patent Application No. PCT/IL03/00913 having International Filing Date of Nov. 3, 2003, which claims the benefit of priority of U.S. Provisional Patent Application No. 60/423,973 filed on Nov. 6, 2002. The contents of the above Applications are all incorporated herein by reference.

FIELD AND BACKGROUND OF THE INVENTION

The present invention relates to measurements of spontaneous and stimulated cell activity and, more particularly, to a method, device and system employing a nano and micro integrated chip for positioning cells and determining cellular electrical and chemical activity, via electrical and/or optical signals.

Improved understanding of complex cell function is important in the fields of science and medicine. One of the key objectives in studies of networks of biochemical reactions is to uncover fundamental principles that govern the cell functioning and the structure and evolution of biological modules. For example, in the discipline of brain research, much effort is devoted to unraveling the rules of formation, function and degeneration of neural networks, which are the linking bridge from neurons to brain.

Many of the crucial studies that led to important understanding of cell function have been conducted in vivo in living animals. It is well recognized that the difficulties encountered using in vivo measurements (e.g., visualization, control of the chemical environment, parallel recording from many cells) are overcome via in vitro settings of tissue slices or cells grown in culture.

Over the past two decades, there has been a tremendous growth in experimental methods that allow for biochemical and biophysical investigations of single cells. Such methods include laser confocal microscopy imaging techniques that can be used to localize bioactive components in single cells and single organelles within cells [S. Maiti et al., *Science*, 275, 530-532, 1997], use of near field optical probes for pH measurements in the cell interior, and the like.

Knowledge of cell activity may also be gained by measuring and recording electrical potential changes occurring within a cell, which changes depend on the type of cells, age of the culture and external conditions such as temperature or chemical environment. Thus, precisely controlling the physical and chemical environment of a cell under study significantly enhances the value of the research. Intracellular and extracellular electrical measurements have application in research studies of nerve cell bodies and tissue culture cells such as smooth muscle, cardiac, and skeletal muscle cells. Such measurements and suitable display of the results thereof are also useful for demonstrations in teaching laboratories.

There are several major different technologies to measure the electrical activity of cells. Known in the art are techniques which are commonly called "patch clamp recordings" [O. P. Hamill et al., *Pfleugers Arch.* 391, 85-100, 1981], which have developed into a very versatile and precise methods. These techniques allow researchers to observe the functioning of a single ionic channel, while monitoring neurons electrical activity in the brain, or allow the monitoring of the change in cell membrane area during a process of secretion, etc. The patch clamp technique provides exquisite resolution for measuring ionic currents in cell membranes, using a glass micropipette having an opening end of the order of 0.1 micron. The micropipette is filled with saline solution and is pressed gently onto the cell membrane, forming a stable physical high resistance electrical seal (in the GigaOhm range) on the cell membrane, commonly termed the Gigaseal. When suction is applied to the micropipette the cell membrane breaks and the cytoplasm and pipette solution start to intermix. Once this mixing is completed, the ionic environment in the cell is similar to the saline filling solution of the micropipette. Ionic currents in the cell membrane are thus indirectly determined by measuring the electrical potential of the solution filling the micropipette.

Another device for measuring the electrical activity of cells is an extracellular electrode, which is a microelectrode being attached to the cell membrane from the extracellular side. The capacitive coupling between the micro-electrode and the cell membrane alter the electrode potential which is used to determine and measure action potentials. As the extracellular electrode is only attached to the cell membrane from the outside, the cell membrane remains intact, and, provided that the appropriate conditions (temperature, PH etc.) are supplied to the cell culture, the cells can survive for weeks [R. Segev, M. Benveniste, Y. Shapira, E. Hulata, N. Cohen, E. Kapon and E. Ben-Jacob, "Long Term Behavior of Lithographically Prepared in vitro Neural Networks", *Phys. Rev. Lett.*, 88: 118102, 2001]. The extracellular signal is about a 1000 fold smaller than the intracellular signal and the noise level in the extracellular domain is of the order of 25 μV. On the other hand, the voltage of synaptic signals is typically lower than 2 μV. Hence, in the extracellular domain, synaptic signals exhibit a signal-to-noise ratio which is insufficient to allow detection of these signals by an extracellular electrode.

Also known in the art is an intracellular electrode entering the cell membrane to measure the intracellular voltage directly [B. Hille, "Ionic channels of excitable membranes", SINAUER, Sunderland, Mass., 1992]. One such intracellular electrode is a fine wire with a sharpened point, where electrical signals which are detected by the sharpened electrode end are amplified, displayed or recorded by equipments electrically coupled to the electrode.

Intracellular electrodes are particularly useful in the elucidation of the single neuron dynamics. The main advantage of intracellular electrodes over the extracellular electrodes and the patch clamp is the high resolution measurements of the cellular voltage which allows studying the effect of a single synapse on a single neuron [H. Markram and M. Tsodyks, *Nature*, 382:807-810, 1996]. However, in this technology, during the measurements the cell membrane is damaged, causing the cellular organs and cytoplasm to diffuse out from the cell and as a result, within several hours (or less) the cell dies. Hence, the presently available intracellular electrodes cannot be used for long period experiments.

Recently, the study of electrical activity in cells has reached a turning point with the development of a multi-electrode-array (MEA) [Y. Jimbo et al., "Simultaneous measurement of intracellular calcium and electrical activity from patterned neural networks in culture", *IEEE Trans. Biom. Egin.*, 40:804-810, 1993; B. C. Wheeler and G. J. Brewer, "Multi-Neuron Patterning and Recording", *Enabling Technologies for Cultured Neuronal Networks*, Editors D. A. Stenger and T. M. McKenna, Academic Press, page 167, 1994; G. J. A. Ramakers et al., "Culturing of Cerebral Cortex Neurons on Multi-Electrode Plates for the Investigation of Long-Term Neuronal Network Development", *International meeting on substrate-integrated microelectrode arrays: technology and applications*, Reutlingen, Germany, Jun. 23-26, 1998, abstract book page 21; M. Camepari et al., "Experimental Analysis of Neuronal Dynamics in Cultured Cortical Networks and Transitions Between Different Patterns of Activity", *Biol. Cyber.*, 77:153-162, 1997].

The MEA is an arrangement of 60 micro-electrodes which are used for parallel for recording the electrical activity of cells in a tissue slice or of cells grown in culture (such as a neural network). The electrodes, typically 10-30 µm in diameter and 50-500 µm apart, are connected to a processing unit via an arrangement of amplifiers. The MEA allows studying the effect of different chemicals or drugs on the electrical activity of the tissue slice or the cells in culture. While measuring the electrical activity via the MEA, other cell characteristics (e.g., the morphology of the cells, chemical activity of the cells, and the like) may be detected by other means, for example, light microscope, etc.

In a typical neural network experiment, a network is composed of about $10^6$ neurons and glial cells, which are grown directly on top of the MEA. Neurons, which are loosely placed above a particular electrode of the MEA form capacitance coupling with that electrode, hence allowing monitoring and recording of both the electrical activity and the electrical stimulation of the neuron.

MEA is also useful in the area of drug discovery where the search for new compounds for clinical use is done by industrialized process. Typically, in a single drug discovery process, many chemical compounds are produced by chemists, where about one tenth of these compounds are qualified for chemical screening. The remaining compounds are further screened in a cell cultural screening, organ screening and animal screening, where in each screening about 9 tenth are disqualified for further research and only one tenth are qualified for further study. Statistically, of the remaining compounds (only about a dozen compounds are left after the above screening procedures) one third are found to achieve the desired clinical goal and only one tenth is approved by the Food and Drug Administration. Hence, the process of discovering a single drug which is eventually approved for clinical use begins with the screening of about one million compounds.

The main goal of each stage in drug discovery is, of course, to estimate the clinical effect of the compound on humans. Hence, experiments are being performed by applying the tested chemical on a model system, first an in vitro system (e.g., cell culture) and then an in vivo system (e.g., intact animals). It is appreciated that the in vivo tests are rather complicated and extremely expansive. Thus, the methodology of screening for new drug candidates demands new methodologies with which to implement efficient and high throughput screening at the early stages, where the compounds are tested in vitro.

Naturally, estimating the effect of a drug on a cell in culture is not an easy task. For example, even if one or more experiments are performed on a single cell, the conclusions from such experiment may not be applicable for a complex living animal or a human being. Thus, it is desired to conduct experiment on complex systems rather than on a single (or a few) cell. The MEA technology has been proposed to facilitate in drugs screening. Typically, however, only about 20 of the 60 electrodes of the MEA show electrical activity. Moreover, often the monitored activity cannot be attributed to a single cell, because more than one cells couples to a single electrode. Hence, although the MEA technology allows for measuring activity of many cells simultaneously, its ability to acquire knowledge on systems which are closer to the in vivo setup is limited.

There is thus a widely recognized need for, and it would be highly advantageous to have, a method, system and device for determining cellular activity devoid of the above limitations.

SUMMARY OF THE INVENTION

According to one aspect of the present invention there is provided a device for positioning at least one cell in at least one addressable position, the device comprising a substrate formed with at least one addressable pore and at least one channel embedded in the substrate and being in fluid communication with the at least one pore, the at least one pore and the at least one channel being designed and constructed such that an under-pressure formed in the at least one channel results in vacuum adherence of the at least one cell onto the at least one pore, such that a single cell is vacuum adhered onto a single pore.

According to further features in preferred embodiments of the invention described below the device comprising a plurality of addressable pores and a plurality of channels and being suitable for positioning a plurality of cells in a plurality of addressable positions.

According to still further features in the described preferred embodiments the at least one cell is a plurality of cells, the at least one pore is a plurality of addressable pores and the at least one channel is a plurality of channels.

According to still further features in the described preferred embodiments the device is designed and constructed locatable on an organ.

According to still further features in the described preferred embodiments the device is designed and constructed locatable on brain.

According to still further features in the described preferred embodiments the device is designed and constructed implantable in an animal.

According to still further features in the described preferred embodiments the substrate is a non-conductive substrate and is further formed with at least one electrode structure, each of the at least one electrode structure is positioned in one of the at least one pore.

According to still further features in the described preferred embodiments the substrate is a non-conductive substrate and is further formed with a plurality of electrode structures, each of the electrode structures is positioned in one of the pores.

According to still further features in the described preferred embodiments the substrate is coated with a coat or having a chemically modified surface, so as to enhance affinity adherence of cells thereto and growth of cells thereon.

According to still further features in the described preferred embodiments the device is designed and constructed such that when a cell adheres to the at least one electrode structure, leakage of intracellular components of the cell is prevented.

According to still further features in the described preferred embodiments the device is designed and constructed such that when a cell adheres to an electrode structure of the plurality of electrode structures, leakage of intracellular components of the cell is prevented.

According to still further features in the described preferred embodiments the substrate is further formed with at least one conductive element embedded therein and electrically coupled to the at least one electrode structure.

According to still further features in the described preferred embodiments the substrate is further formed with a plurality of conductive elements embedded therein, each of the conductive elements is electrically coupled to one of the electrode structures.

According to still further features in the described preferred embodiments the device further comprises a coded interface electrically coupled with the plurality of conductive elements and being connectable to a system of amplifiers.

According to still further features in the described preferred embodiments the device further comprises a system of amplifiers formed on or in the substrate and being electrically coupled with the plurality of conductive elements.

According to still further features in the described preferred embodiments the device further comprises a pump being in fluid communication with the plurality of channels, the pump and each of the plurality of channels being designed and constructed so as to provide an equally distributed pressure drop over the plurality of addressable pores.

According to still further features in the described preferred embodiments the device further comprises a fluid-interface being coupled to a fluid source, for continuously exchanging fluids between the fluid source and the channels and pores.

According to another aspect of the present invention there is provided a system for measuring electrical activity of a plurality of cells, the system comprising, (a) a non-conductive substrate formed with a plurality of addressable pores and a plurality of channels embedded in the substrate and being in fluid communication with the plurality of addressable pores; (b) a plurality of multi-electrode-arrays, each one of the plurality of multi-electrode-arrays includes a plurality of electrode structures formed on a first side of the non-conductive substrate and positioned in one of the pores, and a plurality of conductive elements formed on a second side of the non-conductive substrate, wherein each one of the conductive elements is electrically coupled to one of the electrode structures; and (c) a fluid source being in fluid communication with the plurality of channels; the pores, the channels, the electrode structures and the fluid source are designed and constructed so that the electrode structures sense electrical signals from the plurality of cells while the fluid source continuously exchanges fluids with the channels and pores.

According to further features in preferred embodiments of the invention described below, the plurality of multi-electrode-arrays are arranged so as to reduce ground loops.

According to still further features in the described preferred embodiments the plurality of multi-electrode-arrays are arranged so as to maximize signal-to-noise ratio.

According to still further features in the described preferred embodiments the plurality of multi-electrode-arrays are arranged in a matrix form.

According to still further features in the described preferred embodiments the plurality of multi-electrode-arrays are arranged in a square matrix form.

According to still further features in the described preferred embodiments the non-conductive substrate is coated with a coat or having a chemically modified surface, so as to enhance affinity adherence of cells thereto and growth of cells thereon.

According to still further features in the described preferred embodiments the system further comprises a pump being in fluid communication with the plurality of channels, the pump and each of the plurality of channels being designed and constructed so as to provide an equally distributed pressure drop over the plurality of addressable pores.

According to still further features in the described preferred embodiments the non-conductive substrate is coated with a coat or having a chemically modified surface, so as to enhance affinity adherence of cells thereto and growth of cells thereon.

According to still further features in the described preferred embodiments the system is designed and constructed such that when a cell adheres to an electrode structure of the plurality of electrode structures, leakage of intracellular components of the cell is prevented.

According to still further features in the described preferred embodiments the system further comprises a coded interface electrically coupled with the plurality of conductive elements and being connectable to a system of amplifiers.

According to still further features in the described preferred embodiments the system further comprises a system of amplifiers being electrically coupled with the plurality of conductive elements.

According to still further features in the described preferred embodiments the system of amplifiers are formed on or in the non-conductive substrate.

According to still further features in the described preferred embodiments the system further comprises at least one data processor, electrically coupled to the system of amplifiers viat least one acquisition board, for acquiring and processing data collected from the plurality of electrode structures.

According to still further features in the described preferred embodiments the system further comprises at least one multiplexer, being in electrical communication with the at least one data processor, wherein each one of the at least one multiplexer combines at least two communication channels originated from the acquisition board.

According to still further features in the described preferred embodiments the system further comprises a stimulator electrically communicating with the at least one data processor, for generating temporal stimulating electrical signals, transmitted via the electrode structures to the cells at predetermined intervals and in predetermined durations.

According to yet another aspect of the present invention there is provided a method of positioning at least one cell in at least one addressable position, the method comprising: providing a substrate formed with at least one addressable pore and at least one channel embedded is the substrate and being in fluid communication with the at least one pore; spreading a liquid medium and the at least one cell over the substrate; and generating an under-pressure in the at least one channel so as to adhere the at least one cell onto the at least one pore via vacuum adherence, such that a single cell vacuum adhered onto a single pore, thereby positioning the at least one cell in the at least one addressable position.

According to further features in preferred embodiments of the invention described below, the substrate is formed with a plurality of addressable pores and a plurality of channels and being suitable for positioning a plurality of cells in a plurality of addressable positions.

According to still further features in the described preferred embodiments the method further comprises sensing electrical signals of the cells via a plurality of electrode structures.

According to still further features in the described preferred embodiments the method further comprises amplifying the electrical signals by a system of amplifiers.

According to still further features in the described preferred embodiments the system of amplifiers is formed on or in the substrate.

According to still further features in the described preferred embodiments the method further comprises continuously exchanging fluids between a fluid source and the channels and pores.

According to still another aspect of the present invention there is provided a method of measuring electrical activity of a plurality of cells, the method comprising: (a) providing a non-conductive substrate formed with a plurality of addressable pores and a plurality of channels embedded therein and being in fluid communication with the plurality of addressable pores; (b) spreading a liquid medium and said cells over said substrate; (c) sensing electrical signals of the cells via a plurality of multi-electrode-arrays, wherein each one of the plurality of multi-electrode-arrays includes a plurality of electrode structures formed on a first side of the non-conductive substrate and positioned in one of the pores; and (g) continuously exchanging fluids between a fluid source and the channels and pores a fluid source being in fluid communication with the plurality of channels; thereby measuring the electrical activity of the plurality of cells.

According to further features in preferred embodiments of the invention described below, the sensing electrical signals and the continuously exchanging fluids is executed substantially contemporaneously.

According to still further features in the described preferred embodiments the plurality of cells are electrically excitable.

According to still further features in the described preferred embodiments the plurality of cells are selected from the group consisting of a neuron cell, a heart cell, a muscle cell and a pancreatic cell.

According to still further features in the described preferred embodiments the method further comprises generating an under-pressure in the channels so as to adhere the plurality of cells onto the plurality of addressable pores via vacuum adherence, such that a single cell of the plurality of cells is adhered onto a single pore of the plurality of addressable pores.

According to still further features in the described preferred embodiments the generating the under-pressure is done so as to provide an equally distributed pressure drop over the plurality of addressable pores.

According to still further features in the described preferred embodiments the method further comprises providing a coat or a chemically modified surface to the substrate, selected to enhance affinity adherence of the cells thereto and growth of cells thereon.

According to still further features in the described preferred embodiments the at least one electrode structure is emerging from a base of the at least one pore and protrude from a surface of the non-conductive substrate.

According to still further features in the described preferred embodiments the at least one electrode structure is emerging from a base of the at least one pore and is flush with a surface of the non-conductive substrate.

According to still further features in the described preferred embodiments the electrode structures are emerging from bases of the pores and protrude from a surface of the non-conductive substrate.

According to still further features in the described preferred embodiments the electrode structures are emerging from bases of the pores and are flush with a surface of the non-conductive substrate.

According to still further features in the described preferred embodiments the sensing is by penetrating the cells, using the electrode structures.

According to still further features in the described preferred embodiments the sensing is by externally engaging the cells using the electrode structures.

According to still further features in the described preferred embodiments the at least one electrode structure is substantially perpendicular to the non-conductive substrate.

According to still further features in the described preferred embodiments each of the electrode structures is substantially perpendicular to the non-conductive substrate.

According to still further features in the described preferred embodiments the method further comprises preventing leakage of intracellular components of the cells when the cells adhere to the electrode structures.

According to still further features in the described preferred embodiments the method further comprises administrating at least one substance to the cells via the channels and the pores.

According to still further features in the described preferred embodiments the method further comprises administrating different substances to different cells via the channels and the pores.

According to still further features in the described preferred embodiments the method further comprises amplifying the electrical signals by a system of amplifiers electrically coupled to a plurality of conductive elements formed on a second side of the non-conductive substrate, wherein each one of the conductive elements is electrically coupled to one of the electrode structures.

According to still further features in the described preferred embodiments the method further comprises acquiring and processing data collected from the plurality of electrode structures using at least one data processor.

According to still further features in the described preferred embodiments the method further comprises generating temporal stimulating electrical signals, and transmitting the stimulating electrical signals via the electrode structures to the cells at predetermined intervals and in predetermined durations.

According to still further features in the described preferred embodiments the stimulating is done so as prevent electrolysis process within the electrode structures.

According to an additional aspect of the present invention there is provided a method of manufacturing a device for positioning at least one cell in at least one addressable position, the method comprising providing a substrate and forming therein at least one addressable pore and at least one channel, so that the at least one channel is in fluid communication with the at least one addressable pore, the at least one pore and the at least one channel being designed and constructed such that an under-pressure formed in the channels results in vacuum adherence of the at least one cell onto the at least one addressable pore, such that a single cell is vacuum adhered onto a single pore.

According to further features in preferred embodiments of the invention described below, the method comprising forming in the substrate a plurality of addressable pores and a plurality of channels being suitable for positioning a plurality of cells in a plurality of addressable positions.

According to still further features in the described preferred embodiments the substrate is a non-conductive substrate.

According to still further features in the described preferred embodiments the method further comprises forming, in the at least one pore at least one electrode structure.

According to still further features in the described preferred embodiments the method further comprises forming, in each one of the pores, an electrode structure thereby forming a plurality of electrode structures.

According to still further features in the described preferred embodiments the forming the electrode structures and the forming the pores and the channels is executed substantially contemporaneously.

According to still further features in the described preferred embodiments the forming the electrode structures and the forming the pores and the channels is executed sequentially.

According to still further features in the described preferred embodiments the forming the electrode structures and the forming the pores and the channels is executed in a combination of sequential and substantially contemporaneous steps.

According to still further features in the described preferred embodiments the method further comprises coating the substrate with a coat or forming a chemically modified surface thereon, so as to enhance affinity adherence of cells thereto and growth of cells thereon.

According to still further features in the described preferred embodiments the coat or chemically modified surface is restricted to areas on the substrate surrounding the pores.

According to still further features in the described preferred embodiments the forming the electrode structures is done so that the electrode structures emerge from bases of the pores and protrude from a surface of the substrate.

According to still further features in the described preferred embodiments the forming the electrode structures is done so that the electrode structures are flush with a surface of the substrate.

According to still further features in the described preferred embodiments the forming the electrode structures is done so that the electrode structures are substantially perpendicular to the substrate.

According to still further features in the described preferred embodiments the method further comprises forming at least one conductive element embedded in the substrate and electrically coupling the at least one conductive element to the at least one electrode structure.

According to still further features in the described preferred embodiments the method further comprises forming a plurality of conductive elements embedded in the substrate and electrically coupling each of the conductive elements to one of the electrode structures.

According to still further features in the described preferred embodiments the method further comprises forming a system of amplifiers on or in the substrate and electrically coupling the plurality of conductive elements with the system of amplifiers.

According to still further features in the described preferred embodiments the method further comprises positioning a fluid-interface being coupled to a fluid source, for continuously exchanging fluids between the fluid source and the channels and pores.

According to still further features in the described preferred embodiments the forming the plurality of electrode structures is by patterning a plurality of conductive nuclei onto the conductive elements and growing the electrode structures thereon using a method of plasma enhanced hot filament chemical vapor deposition.

According to still further features in the described preferred embodiments the plurality of conductive nuclei are made of nickel.

According to still further features in the described preferred embodiments the electrode structures are made of carbon.

According to still further features in the described preferred embodiments the method further comprises laminating the conductive elements by a polymer so as to obtain an insulating layer covering the conductive elements and the conductive nuclei.

According to yet an additional aspect of the present invention there is provided a method of manufacturing a system for measuring electrical activity of a plurality of cells, the system comprising: (a) providing a non-conductive substrate and forming therein a plurality of addressable pores and a plurality of channels, so that the plurality of channels are in fluid communication with the plurality of addressable pores; (b) forming a plurality of multi-electrode-arrays on a first side of the non-conductive substrate, each one of the plurality of multi-electrode-arrays includes a plurality of electrode structures, so as to position each one of the electrode structures in one of the pores; (c) forming a plurality of conductive elements on a second side of the non-conductive substrate, so that each one of the conductive elements is electrically coupled to one of the electrode structures; and (d) positioning a fluid source so that the fluid source is in fluid communication with the plurality of channels; the pores, the channels, the electrode structures and the fluid source are designed and constructed so that the electrode structures sense electrical signals from the plurality of cells while the fluid source continuously exchanges fluids with the channels and pores.

According to further features in preferred embodiments of the invention described below, the forming the pores, the channels and the multi-electrode-arrays is done in an arrangement so as to reduce ground loops.

According to still further features in the described preferred embodiments the forming the pores, the channels and the multi-electrode-arrays is done in an arrangement so as to maximize signal-to-noise ratio.

According to still further features in the described preferred embodiments the forming the pores and the multi-electrode-arrays is in a matrix form.

According to still further features in the described preferred embodiments the forming the pores and the multi-electrode-arrays is in a square matrix form.

According to still further features in the described preferred embodiments the forming the pores and the channels, the forming the multi-electrode-arrays and the forming the conductive elements is executed substantially contemporaneously.

According to still further features in the described preferred embodiments the forming the pores and the channels, the forming the multi-electrode-arrays and the forming the conductive elements is executed sequentially.

According to still further features in the described preferred embodiments the forming the pores and the channels, the forming the multi-electrode-arrays and the forming the conductive elements is executed in a combination of sequential and substantially contemporaneous steps.

According to still further features in the described preferred embodiments the non-conductive substrate is designed and constructed locatable on an organ.

According to still further features in the described preferred embodiments the non-conductive substrate is designed and constructed locatable on a brain.

According to still further features in the described preferred embodiments the non-conductive substrate is designed and constructed implantable in an animal.

According to still further features in the described preferred embodiments the non-conductive substrate is flexible.

According to still further features in the described preferred embodiments the pores and the channels are designed and constructed such that an under-pressure formed in the channels results in vacuum adherence of the plurality of cells onto the plurality of addressable pores, such that a single cell of the plurality of cells is adhered onto a single pore of the plurality of addressable pores.

According to still further features in the described preferred embodiments the method further comprises positioning a pump being in fluid communication with the plurality of channels, the pump and each of the plurality of channels being designed and constructed so as to provide an equally distributed pressure drop over the plurality of addressable pores.

According to still further features in the described preferred embodiments the method further comprises coating the substrate with a coat or forming a chemically modified surface thereon, so as to enhance affinity adherence of cells thereto and growth of cells thereon.

According to an additional aspect of the present invention there is provided a method of manufacturing an electrode structure, the method comprising: (a) providing a substrate being of a first type semiconductor material and having a first side and a second side; (b) doping a region on the first side of the substrate by a second type semiconductor material, thereby creating an isolated region of the second type semiconductor; (c) applying an electrically conducting layer on the first side of the substrate, such that the electrically conducting layer is in electrical communication with the region of the second type semiconductor; and (c) growing the electrode structure on the region of the second type semiconductor.

According to further features in preferred embodiments of the invention described below, the method further comprising, prior to the step of applying the electrically conducting layer: passivating the substrate thereby providing a passive layer; and selectively etching the passive layer so as to isolate the region of the second type semiconductor from the passive layer.

According to still further features in the described preferred embodiments the method further comprising passivating the electrically conducting layer.

According to still further features in the described preferred embodiments the passivating is effected by a procedure selected from the group consisting of chemical vapor deposition, physical vapor deposition and spattering.

According to still further features in the described preferred embodiments the method further comprising prior to the step of applying the electrically conducting layer: passivating the first side and the second side of the substrate thereby providing, respectively, a first passive layer and a second passive layer; and selectively etching the first passive layer so as to isolate the region of the second type semiconductor from the first passive layer.

According to still further features in the described preferred embodiments the method further comprising, subsequently to the step of applying the electrically conducting layer: selectively etching the first type semiconductor material; and etching the second passive layer; thereby providing protective walls, surrounding the isolated region of the second type semiconductor.

According to still further features in the described preferred embodiments the growing the electrode structure is effected by a procedure selected from the group consisting of chemical vapor deposition and physical vapor deposition.

According to another aspect of the present invention there is provided a method of manufacturing a device for positioning cells in addressable positions, the method comprising providing a substrate having a first side and a second side, and forming therein at least one addressable pore, the at least one addressable pore is at least partially open from the first side and the second side, such that a flow of cells directed from the first side to the second side, results in at least a partial adherence of the cells onto the at least one addressable pore, wherein each a single cell occupies a single pore.

According to further features preferred embodiments of the invention described below, the substrate is made of a first type semiconductor material.

According to still further features in the described preferred embodiments the forming the at least one addressable pore comprises: doping a region on the first side of the substrate by a second type semiconductor material, thereby creating an isolated region of the second type semiconductor; applying an electrically conducting layer on the first side of the substrate, such that the electrically conducting layer is in electrical communication with the region of the second type semiconductor; and selectively etching the first type semiconductor material; thereby providing protective walls, surrounding the isolated region of the second type semiconductor.

According to still further features in the described preferred embodiments the method further comprising, prior to the step of applying the electrically conducting layer, passivating the first side and the second side of the substrate thereby providing, respectively, a first passive layer and a second passive layer.

According to still further features in the described preferred embodiments the method further comprising, subsequently to the step of applying the electrically conducting layer: selectively etching the first passive layer so as to isolate the region of the second type semiconductor from the first passive layer.

According to still further features in the described preferred embodiments the method further comprising, subsequently to the step of selectively etching the first type semiconductor material, etching the second passive layer.

According to still further features in the described preferred embodiments the electrode structure is grown on the region of the second type semiconductor.

According to still further features in the described preferred embodiments the first type semiconductor material is an n-type semiconductor material and the second type semiconductor material is a p-type semiconductor material.

According to still further features in the described preferred embodiments the first type semiconductor material is a p-type semiconductor material and the second type semiconductor material is an n-type semiconductor material.

According to still further features in the described preferred embodiments the passivating is effected by a procedure selected from the group consisting of oxidation, chemical vapor deposition, physical vapor deposition and spattering.

According to still further features in the described preferred embodiments the coat or chemically modified surface is patterned.

According to still further features in the described preferred embodiments the coat or chemically modified surface is discontinuous.

According to still further features in the described preferred embodiments the coat or chemically modified surface is restricted to areas on the non-conductive substrate surrounding the pores.

According to still further features in the described preferred embodiments the forming the multi-electrode-arrays is done so that the electrode structures emerge from bases of the pores and protrude from a surface of the substrate.

According to still further features in the described preferred embodiments the forming the multi-electrode-arrays is done so that the electrode structures are flush with a surface of the substrate.

According to still further features in the described preferred embodiments the at least one electrode structure is designed and constructed to penetrate into a cell adhered thereto.

According to still further features in the described preferred embodiments each of the electrode structures is designed and constructed to penetrate into a cell adhered thereto.

According to still further features in the described preferred embodiments the at least one electrode structure is designed and constructed to externally engage a cell adhered thereto.

According to still further features in the described preferred embodiments each of the electrode structures is designed and constructed to externally engage a cell adhered thereto.

According to still further features in the described preferred embodiments the forming the multi-electrode-arrays is done so that the electrode structures are substantially perpendicular to the substrate.

According to still further features in the described preferred embodiments the electrode structures have hydrophobic properties.

According to still further features in the described preferred embodiments the channels and the pores are designed and constructed so as to allow administration therethrough of at least one substance to the cells.

According to still further features in the described preferred embodiments the channels and the pores are designed and constructed so as to allow administration therethrough of different substances to different cells of the plurality of cells.

According to still further features in the described preferred embodiments the plurality of conductive elements and the plurality of channels are devoid of electrical coupling thereamongst.

According to still further features in the described preferred embodiments the plurality of conductive elements and the plurality of channels are formed at different layers within the non-conductive substrate.

According to still further features in the described preferred embodiments the method further comprises electrically coupling a coded interface with the plurality of conductive elements, the coded interface being connectable to a system of amplifiers.

According to still further features in the described preferred embodiments the method further comprises positioning a system of amplifiers and electrically coupling the plurality of conductive elements with the system of amplifiers.

According to still further features in the described preferred embodiments the method further comprises forming or a system of amplifiers on or in the substrate and electrically coupling the plurality of conductive elements with the system of amplifiers.

According to still further features in the described preferred embodiments the coded interface comprises a plurality of transmission lines, each transmission line being electrically coupled to one of the plurality of conductive elements.

According to still further features in the described preferred embodiments the method further comprises providing at least one data processor, and electrically coupling the at least one data processor to the system of amplifiers viat least one acquisition board.

According to still further features in the described preferred embodiments the method further comprises providing at least one multiplexer, being in electrical communication with the at least one data processor, wherein each one of the at least one multiplexer combines at least two communication channels originated from the acquisition board.

According to still further features in the described preferred embodiments the method further comprises providing a stimulator electrically communicating with the at least one data processor, for generating temporal stimulating electrical signals, transmitted via the electrode structures to the cells at predetermined intervals and in predetermined durations.

According to still further features in the described preferred embodiments the stimulator is designed and configured so as prevent electrolysis process within the electrode structures.

According to still further features in the described preferred embodiments each of the electrode structures is characterized by voltage sensitivity ranging from 1 microvolt to 1 volt.

According to still further features in the described preferred embodiments the voltage sensitivity is selected so as to allow sensing extracellular potentials.

According to still further features in the described preferred embodiments the voltage sensitivity is selected so as to allow transmitting stimuli to the cells.

According to still further features in the described preferred embodiments the voltage sensitivity is selected so as to allow sensing intracellular potentials.

According to still further features in the described preferred embodiments each of the plurality of conductive elements is made of Gold.

According to still further features in the described preferred embodiments the coating the substrate with the coat or forming the chemically modified surface thereon comprises: coating the substrate by a photoresist layer, patterning the photoresist layer, immersing the substrate in a solution containing a coating substance and removing the photoresist layer.

According to still further features in the described preferred embodiments the coating substance is selected from the group consisting of a protein, a peptide and a carbohydrate.

According to still further features in the described preferred embodiments the coating substance is selected from the group consisting of Poly-D-Lysine, Poly-D-Arginine, a mixed polymer of D-Lysine and D-arginine and Glc-Nac.

According to still further features in the described preferred embodiments the forming the at least one conductive element is by micro-lithography.

According to still further features in the described preferred embodiments the forming the plurality of conductive elements is by micro-lithography.

According to still further features in the described preferred embodiments the forming the at least one addressable pore and the at least one channel is by micro-lithography.

According to still further features in the described preferred embodiments the forming the plurality of addressable pores and the plurality of channels is by micro-lithography.

According to still further features in the described preferred embodiments the forming the at least one addressable pore and the at least one channel comprises laminating a first layer of a first polymer on the substrate, structuring the first layer by photolithography so as to shape the at least one channel and the at least one pore and laminating a second layer of a second polymer on the at least one channel.

According to still further features in the described preferred embodiments the forming the plurality of addressable pores and the plurality of channels comprises laminating a first layer of a first polymer on the substrate, structuring the first layer by photolithography so as to shape the channels and the pores and laminating a second layer of a second polymer on the channels.

According to still further features in the described preferred embodiments the first polymer is Riston®.

According to still further features in the described preferred embodiments the second polymer is Riston®.

According to still further features in the described preferred embodiments the first polymer is SU-8.

According to still further features in the described preferred embodiments the forming the plurality of multi-electrode-array is by photolithography and lift-off technique.

According to still further features in the described preferred embodiments the forming the plurality of multi-electrode-array comprises: (i) applying a first metal layer on the non-conductive substrate; (ii) patterning the metal layer by photolithography, thereby providing a first patterned metal layer; (iii) applying an insulating layer on the first patterned metal layer; (iv) patterning the insulating layer by photolithography, thereby providing a patterned insulating layer; and (v) applying a second metal layer on the patterned insulating layer using lift-off technique.

According to still further features in the described preferred embodiments the first metal layer is made of Titanium and Gold.

According to still further features in the described preferred embodiments the second metal layer is made of Titanium Nitride.

According to still further features in the described preferred embodiments the insulating layer is made of Silicon Nitride.

According to still further features in the described preferred embodiments the electrode structures are a nanotubes characterized by an inner diameter of 5 nm to 20 nm, an outer diameter of 50 nm to 200 nm and a height of 100 nm to 5000 nm.

According to still further features in the described preferred embodiments an average separation between two electrode structures is from 50 nm to 300 nm.

According to still further features in the described preferred embodiments the electrode structures are characterized by an outer diameter of 10 micrometers to 30 micrometers.

According to still further features in the described preferred embodiments an average separation between two electrode structures is from 50 micrometers to 300 micrometers.

According to still further features in the described preferred embodiments each of the channels is characterized by an inner diameter of 10 micrometers to 50 micrometers.

The present invention successfully addresses the shortcomings of the presently known configurations by providing a method of and a system for positioning cells and determining cellular activity thereof which enjoy properties far exceeding prior art properties.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 5:
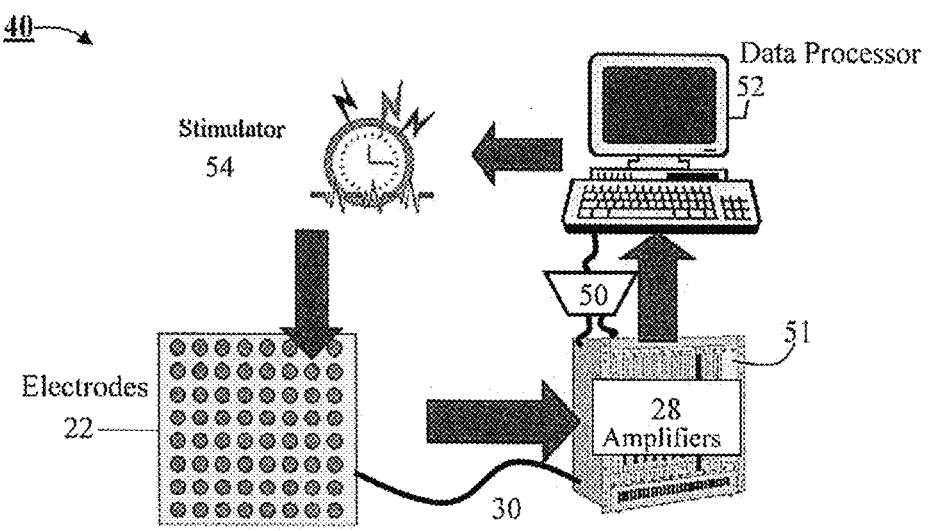
Figure 6A:
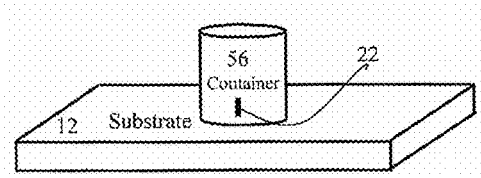
Figure 6B:
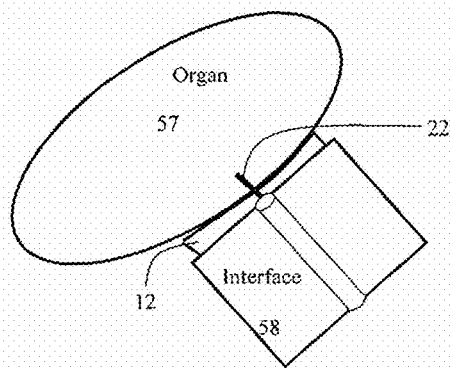
Figure 7:
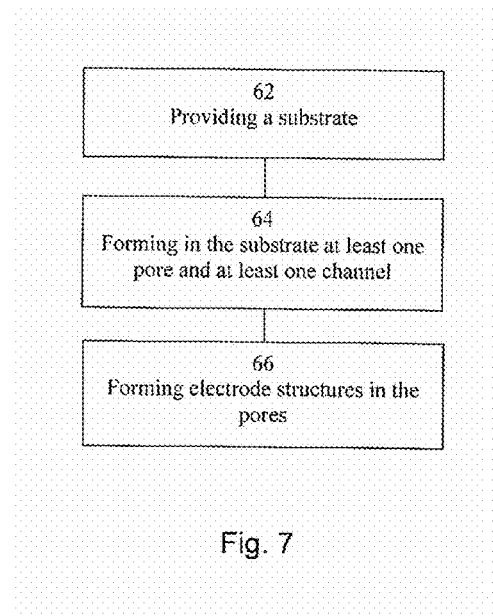
Figure 8:
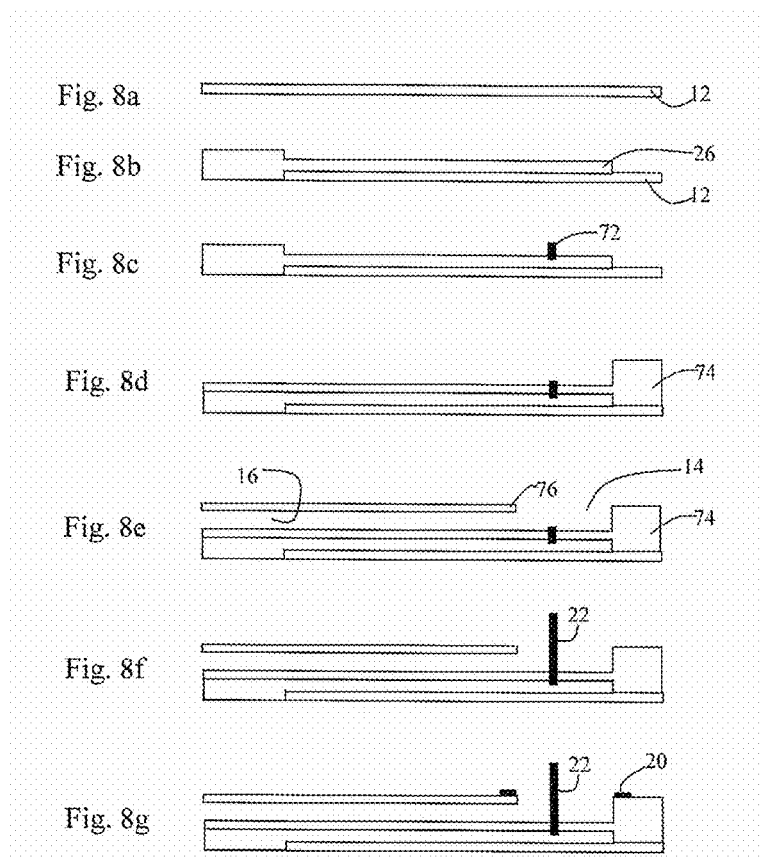
Figure 9:
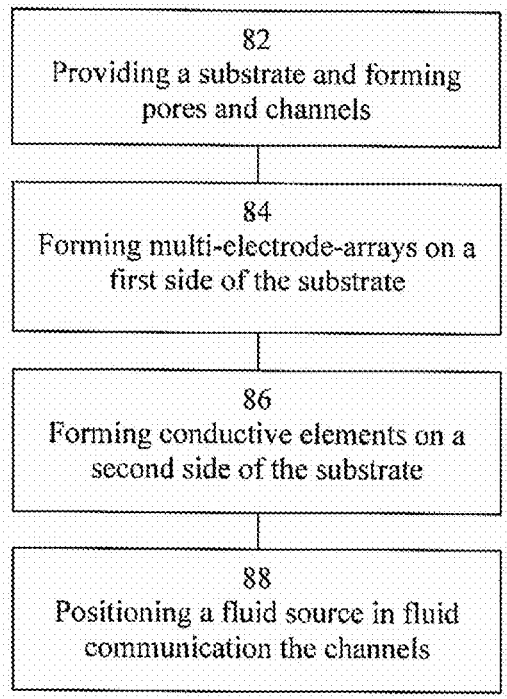
Figure 10:
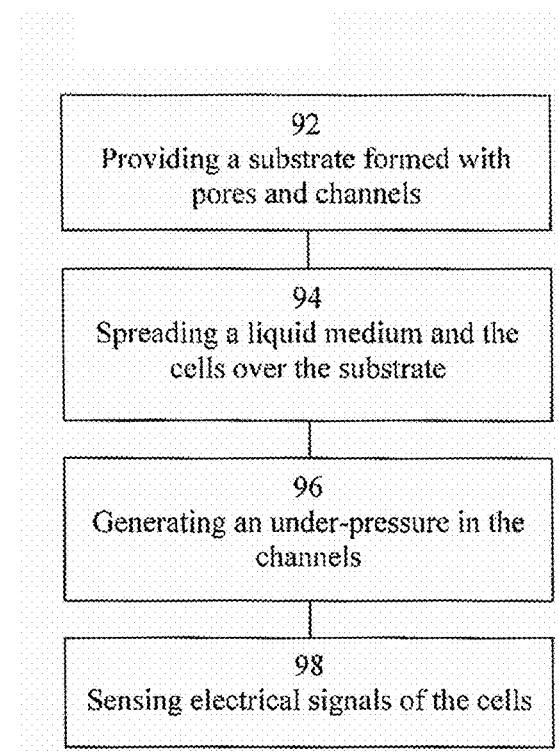
Figure 11:
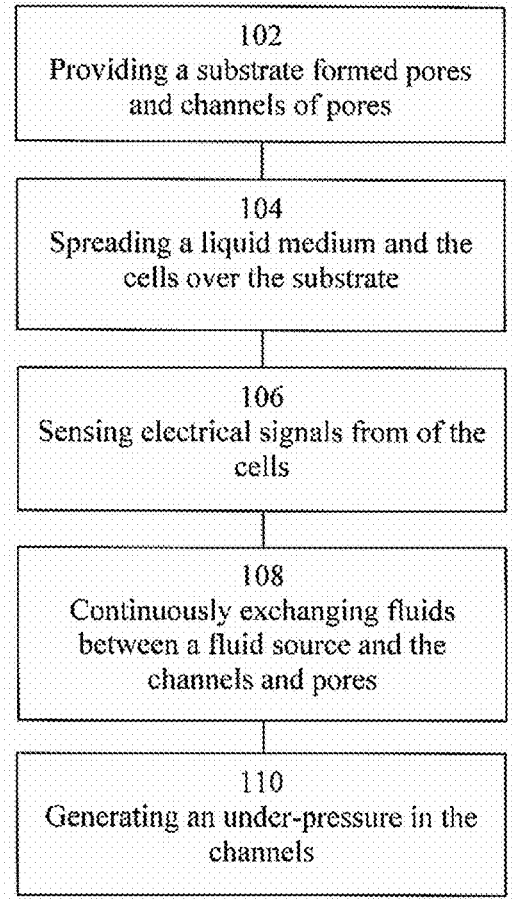

FIGS. 1a-b are schematic illustrations of a top view and a side view of a device for positioning a plurality of cells in a plurality of addressable positions, according to the present invention;

FIG. 2 is a schematic illustration of system for measuring electrical activity of a plurality of cells, according to the present invention;

FIGS. 3a-c are enlarge illustrations of a multi-electrode-array employed by the system of the present invention;

FIGS. 4a-c illustrate the multiplicity of multi-electrode-arrays employed by the system of the present invention;

FIG. 5 is a schematic illustration of system which further comprises amplifiers, a stimulator and data processors, according to the present invention;

FIG. 6a shows a possible in vitro use of the device and the system, according to the present invention;

FIG. 6b shows a possible in vivo use of the device and the system, according to the present invention;

FIG. 7 is a flowchart diagram of a method of manufacturing a device for positioning a plurality of cells in a plurality of addressable positions, according to the present invention;

FIGS. 8a-g is a schematic illustration of a protocol for forming the conductive elements, channels, pores, electrode structures and a coat, according to the present invention;

FIG. 9 is a flowchart diagram of a method of manufacturing a system for measuring electrical activity of a plurality of cells, according to the present invention;

FIG. 10 is a flowchart diagram of a method of positioning a plurality of cells in a plurality of addressable positions, according to the present invention;

FIG. 11 is a flowchart diagram of a method of measuring the electrical activity of a plurality of cells, according to the present invention.

Figure 13:
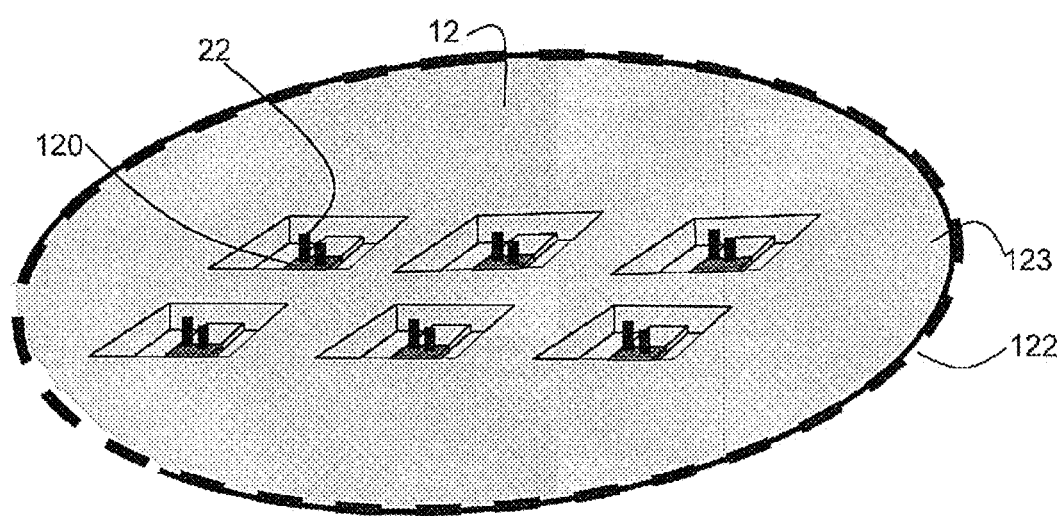

FIG. 12a-i are schematics illustration of method steps for manufacturing an electrode structure on a substrate, in a manner that while the electrode structure is electrically isolated from the substrate, and electrically coupled to a conductive layer applied on the substrate from below, according to the present invention; and FIG. 13 is a schematic illustration of a substrate with electrode structures manufactured according to the method steps of FIGS. 12a-i, according to the present invention.

DESCRIPTION OF THE PREFERRED EMBODIMENTS

The present invention is of a method, system and device for determining the activity of cells engaged in addressable positions, which can be used for studying interactions among cells. Specifically, the present invention can be used to monitor and study functionality, development and morphology of cells, e.g., electrically excitable cells. The present invention is further of a method and device for positioning cells in addressable positions.

The principles and operation of the device, system and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed here it is for the purpose of description and should not be regarded as limiting.

Referring now to the drawings, FIGS. 1a-b illustrate a top view (FIG. 1a) and a side view (FIG. 1b) of a device for positioning at least one cell 18 in at least one addressable position, generally referred to herein as device 10.

Device 10 comprises a substrate 12 formed with at least one addressable pore 14 and at least one channel 16 embedded in substrate 12, and in fluid communication with addressable pore 14. According to a preferred embodiment of the present invention device 10 preferably comprises a plurality of addressable pores and a plurality of channels, which are suitable for positioning a plurality of cells in a plurality of addressable positions.

Hence, pores 14 and channels 14 are designed and constructed such that an under-pressure formed in channels 16 results in vacuum adherence of cells 18 onto pores 14. With reference to FIG. 1b, a single cell of cells 18 is adhered onto a single addressable pore of the plurality of addressable pores 14.

According to a preferred embodiment of the present invention substrate 12 is coated with a coat 20 or, alternatively, substrate 12 may have a chemically modified surface 21. Coat 20 facilitates an enhance affinity adherence of cells 18 to substrate 12 and growth of cells 18 thereon. Coat 20 (or chemically modified surface 21) may be applied on substrate 12 in more than one form, for example, coat 20 may be patterned, either continuously or discontinuously over surface 20.

Coat 20 (or chemically modified surface 21) may include more than one substance, so that one substance (for example a substance which facilitates growth) is continuously distributed over surface 12 and another substance (for example a substance which facilitates affinity adherence) is discontinuously patterned over surface 12. According to a preferred embodiment of the present invention, coat 20 is restricted to areas on substrate surrounding pores 14 so that positions of cells 18 onto pores 14 are favored over other positions on substrate 12. Thus, in this embodiment, the positioning and the adhering of cells 18 to the addressable positions is achieved both by mechanical forces generated by the under-pressure in channels 16 and by the affinity binding of cells 18 to coat 20. Coat 20 may be any coat known to have affinity to the cells of interest, for example, a protein, a peptide or a carbohydrate. Substrates which may be used for coat 20 include, but are not limited to, Poly-D-Lysine, Poly-D-Arginine, a mixed polymer of D-Lysine and D-arginine and Glc-Nac.

Once positioned on device 10, cells 18 may be further analyzed and studied both optically (e.g., using an optical apparatus such as, but not limited to, a microscope or a spectral imaging apparatus) and electrically by detecting electrical signals from and/or sending electrical stimuli to cells 18.

Hence, according to a preferred embodiment of the present invention, substrate 12 is non-conductive so as to allow device 10 to incorporate therein means for detecting/transmitting electrical signals. In this embodiment, substrate 12 is further formed with at least one electrode structure 22, emerging from a base 24 of a pore 14, preferably substantially perpendicularly to substrate 12. In embodiments of the present invention characterized by a plurality of pores, substrate 12 is further formed with a plurality of electrode structures 22, emerging from bases 24 of pores 14, again, preferably substantially perpendicularly to substrate 12.

As further detailed hereinunder, pores 14 may be at least partially open on both sides of substrate 12, so as to allow flow of cells present in a solution therethrough, thereby further enhancing the ability of device 10 to position cell 18 in pores 14.

The dimensions of electrode structures 22 are selected in accordance with the application for which device 10 is employed. Thus, in one embodiment the electrode structures 22 protrude from the surface of substrate 12, so that electrode structures 22 penetrate into cells 18 once located thereabove. In other words, the height of electrode structures 22 is selected such that electrode structures 22 become suitable to serve as intracellular electrodes. Any kind of intracellular electrodes may be used, for example micro-tubules, conductive whiskers, conductive nanotubes, conductive microelectrodes and the like. An example of a protocol for fabricating electrode structures 22 is given hereinafter. According to the presently preferred embodiment of the invention, device 10 is constructed to prevent leakage of intracellular components of cells 18 once adhered to electrode structures 22. This may be done by a judicious selection of (i) the external diameter of electrode structures 22; (ii) the material of which electrode structures 22 are formed; (iii) the residual height of electrode structures 22 above substrate 22; (iv) the magnitude of the attraction forces caused by the under-pressure in channels 16; and (v) the flow rate of cells through device 10, in the embodiment in which pores 14 are partially open. More particularly, electrode structures 22 preferably have hydrophobic properties and an average diameter of nanometer scale, so that the membranes of cells 18, which are known to be hydrophobic bilipid layers, are sealed on electrode structures 22 thereby preventing the cytoplasm and the cellular organs from diffusing out of cells 18. In addition, the pressure drop in channels 16 and the residual height of electrode structures 22 above substrate 22 are preferably selected sufficiently small so that when cells 18 are in contact with electrode structures 22 the membranes are pierced, yet not damaged.

In another embodiment, electrode structures 22 are substantially flash with substrate 12, so that electrode structures 22 externally engage cells 18. Hence, in this embodiment electrode structures 22 serve as extracellular electrodes.

Depending on whether electrode structures 22 operate as intracellular or extracellular electrodes, the voltage sensitivity of electrode structures 22 varies so as to allow sensing intracellular potentials (in the embodiments in which electrode structures 22 penetrate into cells 18) or extracellular potentials (in the embodiments in which electrode structures 22 externally engage cells 18). Typically, the voltage sensitivity of electrode structures 22 may vary from 1 microvolt to 1 volt.

According to a preferred embodiment of the present invention device 10 further comprises a plurality of conductive elements 26 embedded in substrate 12, and electrically coupled to electrode structures 22. Conductive elements 26 may be fabricated from any conductive material such as, but not limited to, Gold. Preferably, conductive elements 26 and channels 16 are devoid of electrical coupling thereamongst, for example, by forming conductive elements 26 and channels 16 at different layers within non-conductive substrate 12. Conductive elements 26 serve for transmitting therethrough the electrical stimuli sent by some stimulator or the electrical signals sensed by electrode structures 22. According to a preferred embodiment of the present invention, conductive elements 26 are connected to a system of amplifiers 28 which may be either external amplifiers or, alternatively, internal amplifiers, integrally formed on or in substrate 22. Amplifiers 28 serve for amplifying the electrical signals to a level which is suitable for further processing or recording of the acquired data. The connection between conductive elements 26 and amplifiers 28 is preferably via a coded interface 30, e.g., a plurality of transmission lines, where each transmission line is electrically coupled to one conductive element.

As stated, channels 16 facilitate the vacuum adherence of cells 18 to pores 14, by the under-pressure formed in channels 16 and pores 14. The under-pressure may be provided by any known way, for example, by a pump 32, being in fluid communication with channels 16. Pump 32 and channels 16 are preferably constructed and designed so that the pressure drop at each pore is equally distributed, thus maintaining constant adhesive forces between cells 18 and pores 14. This can be achieved, for example, by providing channels 16 with different and/or changing diameters.

While conceiving the present invention it has been realized that channels 16 may also be utilized for the purpose of delivering fluids to and from cells 18. Such fluids delivery may be exploited for providing constant or controlled conditions to the examined cell culture, e.g., by supplying nutrition and a variety of substances to cells 18 and frequently refreshing the extracellular environment. Thus, according to a preferred embodiment of the present invention device 10 is coupled, via a fluid-interface 34, to a fluid source 36 for continuously exchanging fluids between fluid source 36 and channels 16 and pores 14. In this embodiment, channels 16 mimic the functionality of the heart and lungs in an in vivo environment, thereby providing a significant added value to any in vitro experiment employing device 10.

In another embodiment, channels 16 are used for administrating substances to cells 18 via pores 14. It will be appreciated that since device 10 is directed at positioning cells 18 in addressable positions, different substances may be administrated to different addressable positions so that the study of the effect(s) of these substances on the functionality of cells 18 may have a local addressable nature.

According to another aspect of the present invention there is provided a system for measuring electrical activity of a plurality of cells, generally referred to herein as system 40. System 40 combines selected features of device 10 (e.g., pores 14 and channels 16) together with a plurality of multi-electrode-arrays. Multi-electrode-arrays are known in the art and have already been introduced in the Background section hereinabove.

In prior art multi-electrode-arrays, however, the electrical contacts are on the periphery of the carrying device, resulting in a multi-electrode-array width which grows linearly with the number of electrodes. It is recognized that the size of a multi-electrode-array plays an important role both in the production process of the multi-electrode-array and in data acquisition therefrom. Specifically, the size of a multi-electrode-array affects the use and/or manufacture of a plurality of multi-electrode-arrays within a single device, where small size multi-electrode-arrays are more suitable for constructing an integrated system employing a plurality of multi-electrode-arrays.

As further described below, with reference to FIGS. 2-5, the present invention successfully provides a practical and simple solution to the problem of combining a plurality of multi-electrode-arrays by an economic arrangement of the conductive elements substantially underneath the detection zone of the multi-electrode-array.

Reference is now made to FIG. 2, which is schematic illustration of a system 40. System 40 comprises a non-conductive substrate 12 formed with pores 14 and channels 16 as further detailed hereinabove with respect to pores 14 and channels 16 of device 10. System 40 further comprises a plurality of multi-electrode-arrays 42, each composed of a plurality of electrode structures 22 which are positioned in pores 14, similarly to the positions of electrode structures 22 in device 10.

FIGS. 3*a-c* are enlarged illustrations of one of multi-electrode-arrays 42, where FIG. 3*a* is an isometric view, FIG. 3*b* is a top view and FIG. 3*c* is a bottom view, each shows, in addition to electrode structures 22, a plurality of conductive elements 26 which are formed on substrate 12. However, unlike prior art multi-electrode-arrays, according to this embodiment of the present invention, electrode structures 22 are formed on a first side 44 of substrate 12 and conductive elements 26 are formed on a second side 46 of substrate 12. One of ordinarily skill in the art would appreciate, that the positioning of conductive elements 26 and electrode structures 22 on opposite sides of substrate 12 significantly reduces the size of each multi-electrode-array thereby allowing efficient integration of a plurality of multi-electrode-arrays.

With reference now to FIG. 4, the multiplicity of electrode structures 22 in multi-electrode-arrays 42 is substantially enhanced. According to a preferred embodiment of the present invention, the number of multi-electrode-arrays is from about 50 to about 100 and the number of electrode structures 22 in each multi-electrode-array is from about 50 electrode structures to about 100 electrode structures. Hence, system 40 can be used for simultaneously stimulating and/or sensing signals from a large number of cells, which is higher than prior art multi-electrode-arrays by more than one magnitude of order.

Multi-electrode-arrays 42 are preferably arranged so as to minimize the total engaged area thereby reducing ground loops and maximizing signal-to-noise ratio. This may be done, for example, by arranging multi-electrode-arrays 42 in a matrix (e.g., a square matrix) form.

Referring again to FIG. 2, system 40 further comprises fluid source 36 which is in fluid communication channels 16, similarly to the respective embodiments of device 10. Each one of electrode structures 22 is positioned in one pore so that system 40 allows for stimulating the cells and/or sensing electrical signals thereof, while at the same time continuously exchanging fluids between fluid source 36 pores 14 and channels 16, as further detailed hereinabove. Thus, system 40 combines the features that mimic the functionality of the heart and lungs of device 10 and the enhanced multiplicity of electrode structures 22.

According to a preferred embodiment of the present invention, pores 14 and channels 16 are designed and constructed such that an under-pressure formed in channels 16 (e.g., by pump 32) results in vacuum adherence of the cells onto pores 14, as further detailed hereinabove. Thus, in this embodiment, system 40 enjoys properties of stimulating and/or sensing electrical signals from a large number of cells being in addressable positions.

With reference now to FIG. 5, the data acquisition from electrode structures 22 is preferably designed so as to incorporate simultaneous acquiring, amplifying and processing of large number of signals from different electrodes.

Hence, system 40 preferably comprises coded interface 30 and/or a system of amplifiers 28 for amplifying the electrical signals. Still preferably, amplifiers 28 are integrated on a single (or a few) acquisition board 51, so as to avoid the need of external boxes housing electronic devices which causes undesired ground-loops. Similarly to device 10 amplifiers may be formed directly onto substrate 12 for further reducing noise from excessive wiring.

According to a preferred embodiment of the present invention system 40 may further comprise at least one data processor 52 for processing and, optionally, recording the data. It would be appreciated that the number of data processor may vary, depending on (i) the total number of electrode structures 22; and (ii) the capability of each data processor to acquire parallel signals. Specifically, if data processor 52 is capable of acquiring and processing all the signals from amplifiers 28, system 40 may include one data processor. Alternatively, if data processor 52 is capable of acquiring and processing data from a portion of amplifiers 52, several data processors are used, where each data processor acquires and processes a portion of the data, and each portion is associated with a subgroup of electrode structures 22 or multi-electrode-arrays 42.

System 40 may further comprise a stimulator 54 for generating temporal stimulating electrical signals, which are transmitted via electrode structures 22 to the cells, at predetermined intervals and in predetermined durations. A typical duration of a stimulating signal is from about 100 microseconds to about 300 microseconds.

According to a preferred embodiment of the present invention stimulator 54 is designed and configured so as prevent electrolysis process within electrode structures 22. Preferably, stimulator 54 is controlled by data processor 52 so that the acquisition of electrical signals from electrode structures 22 is separated from the generation of stimulating signals by stimulator 54.

According to a preferred embodiment of the present invention the communication between amplifiers 28 and data processor 52 is viat least one multiplexer 50 designed for combining several communication channels. Presently available multiplexers are known to combine about 100 communication channels into a single high rate communication channel. It is to be understood, however that other multiplexers which will be developed during the lifetime of this patent are also within the scope of the present invention. Hence, the use of multiplexers facilitates parallel communication between amplifiers 28 and data processor 52.

It is to be understood, that in all the above embodiments, the coupling between electrode structures 22 and the cells of interest is not limited to be performed in vitro and that it can also be done in vivo, both in system 40 and in device 10. More particularly, with reference to FIG. 6a, for in vitro measurement, the cells are directly spread onto substrate 12, or being held in a container 56 so that the cell culture medium is in contact with electrode structures 22. With reference to FIG. 6b, for in vivo measurement, substrate 12 is attached to an organ 57 of an animal (e.g., a brain) so that the cells are in contact with substrate 12. In this embodiment, substrate 12 is preferably compact and/or flexible, and it may be connected to an interface 58 facilitating the formation of the under-pressure, the electrical transfer and/or the administration of substances as further detailed hereinabove. According to a preferred embodiment of the present invention, substrate 12 and/or device 10 may also be designed and constructed implantable in an animal.

Reference is now made to FIG. 7, which is a flowchart diagram of a method of manufacturing a device for positioning at least one cell in at least one addressable position (e.g., device 10), according to an additional aspect of the present invention.

The method comprising the following method steps in which is a first step, represented by Block 62, a substrate (e.g., substrate 12) is provided, and in a second step, represented by Block 64, the substrate is formed with at least one addressable pore and at least one channel, so that a respective channel is in fluid communication with a respective pore. The pore and the channel are designed and constructed such that an under-pressure formed in the channel results in vacuum adherence of the cell onto the pore, as further detailed hereinabove.

Techniques of forming pores and channels in a substrate are known in the art and several protocols have been proposed for such formations [to this end see, e.g., Heusckel, M. O. et al., "Buried microchannels in photopolymer for delivering of solutions to neurons in a network", *Sensors and Actuators* B 48:356-361, 1998]. For example, the pores and the channels may be formed by micro-lithography, as further detailed hereinafter with reference to FIG. 8.

According to a preferred embodiment of the present invention the method further comprises an optional step of coating the substrate with a coat, (e.g., coat 20) or, alternatively, forming a chemically modified surface on the substrate. The coat (or the chemically modified surface) is selected so as to enhance affinity adherence of cells to, and growth of cells on the substrate.

Protocols of providing such a coat are known. For example, a protocol of patterning the substrate with Poly-D-Lysine (PDL) may include the steps of coating (e.g., by spinning) the surface of the substrate by a photoresist layer, exposing and developing the photoresist layer through a patterned mask, and immersing the substrate in a PDL water solution. Once a layer of PDL is formed, the substrate is immersed in an ultrasonic acetone bath, to remove the photoresist layer, leaving the coat on the photoresist-free areas of the substrate.

In the embodiments in which the device is used for measuring electrical activity of the cells, the method preferably comprises an additional optional step, represented by Block 66, in which the substrate is further formed with a plurality of electrode structures (e.g., electrode structures 22) in the pores for sensing and/or transmitting electrical signals of and to the cells. In this embodiment the method preferably further comprises additional optional steps in which a plurality of conductive elements are formed in the substrate and are electrically coupling to the electrode structures.

It is to be understood, that it is not intended to limit the invention to any specific order of steps. Thus, the formation steps of the method (channels formation, pores formation electrode structures formation and/or conductive elements formation) may be executed, either sequentially, in any order, or contemporaneously. In addition, some formation steps may be executed sequentially while other formation steps may be executed contemporaneously.

Reference is now made to FIGS. 8a-g, which illustrate an optional and preferred protocol for forming conductive elements 26, channels 16, pores 14, electrode structures 22 and coat 20 in substrate 12.

Hence in FIG. 8a substrate 12 is provided and in FIG. 8b surface 12 is coated and patterned by a conductive material (e.g., Gold) to form conductive elements 26.

In FIG. 8c one or more conductive nuclei 72 are patterned onto conductive elements 26. Conductive nuclei 72 serve as a seed for growing electrode structures 22, may be of any material known to have sufficient adherence properties with conductive elements 26 and which can facilitate growing of electrode structures 22 therefrom. One example of such a material is Nickel.

In FIG. 8d a first layer 74 of a first polymer is laminated and structured by photolithography so as to shape the channels and the pores. Nickel is known to be toxic to cells. Thus, according to a preferred embodiment of the present invention the thickness of first layer 74 is selected such that a substantial portion of the height of nuclei 72 is covered by the first polymer, so as to provide isolating layer between nuclei 72 and the cells.

In FIG. 8e a second layer 76 of a second polymer is laminated to form channels 16. The first and the second polymers may each independently be any known polymers suitable for micro-lithography techniques, such as, but not limited to, Riston® or SU-8.

In FIG. 8f, electrode structures 22 are grown on nuclei 72. Electrode structures 22 may be of any conductive material which can be grown on nuclei 72 such as, but not limited to, Carbon. The growth of electrode structures 22 may be facilitated using any technique known in the art for such a process. For example, one such process is known as plasma enhanced hot filament chemical vapor deposition, and is found, e.g., in an article by Z. F. Ren et al., entitled "Growth of single Freestand Multiwall Carbon Nanotube on Each Nanonickel Dot", and published in *Applied Physics Letters*, volume 75 pages 1086-1088, 1999. In this method an array of individual multiwall carbon nanotubes are grown onto a grid of patterned Nickel. The growth of electrode structures 22 is facilitated by loading nuclei 72 into a plasma-enhanced-hot-filament system [Z. F. Ren et al., *Science* 282:1105 (1998); Z. P. Huang et al., *Applied Physics Letters*, 73:3845 (1998); Z. F. Ren et al., *Proceedings of* 13th *International Winter School on Electronic Properties of Novel Materials*, Kirchberg/Tirol, Austria, 1999], with an acetylene ammonia mixture. Typical growth time of this process is about 5 minutes.

In FIG. 8g, coat 20 is patterned onto substrate 22 in restricted areas, preferably surrounding pores 14 and electrode structures 22.

Additional optional and preferred steps of the method include any combination of the following steps: electrically coupling a coded interface with the conductive elements, forming a system of amplifiers on or in the substrate and positioning a pump and/or a fluid source being in fluid communication with the channels.

Reference is now made to FIG. 9, which is a flowchart diagram of a method of manufacturing a system for measuring electrical activity of a plurality of cells (e.g., system 40), according to yet an additional aspect of the present invention.

The method comprising the following method steps in which is a first step, represented by Block 82 a substrate (e.g., substrate 12) is provided and formed with a plurality of addressable pores and a plurality of channels, as further detailed hereinabove.

In a second step, represented by Block 84 a plurality of multi-electrode-arrays are formed on a first side of the substrate, where each one of the multi-electrode-arrays includes a plurality of electrode structures.

In a third step, represented by Block 86, a plurality of conductive elements are formed on a second side of the substrate, so that each conductive element is electrically coupled to one electrode structure.

In a fourth step, represented by Block 88, a fluid source is positioned so that the fluid source is in fluid communication with the channels. As already stated, in operation mode, the fluid source serves for continuously exchanging fluids with the channels and the pores, during the determination of the electrical activity of the cells.

The second and third steps of the method in which the multi-electrode-arrays and the conductive elements are formed on the substrate may be done in more than one way. Hence, in one embodiment, each electrode structure is formed within a pore and in contact with one conductive element, as detailed hereinabove with reference to FIG. 8. In this embodiment, the conductive elements preferably protrude downwards from the substrate, so as to minimize the area which is occupied by the conductive elements.

An alternative method of forming the multi-electrode-array, in accordance with another embodiment of the present invention, is described in an article by Egert, B. et al., entitled "A Novel Organotypic Long-Term Culture of the Rat Hippocampus on Substrate-Integrated Multi-Electrode-Arrays", published in *Brain Research Protocols*, volume 2 pages 229-242, 1998.

In this embodiment, the substrate is deposited by a metal, preferably Titanium followed by Gold, by acceleration of particles within a vacuum tube. The selection of Titanium and Gold is due to the known properties of these metals to adhere to each other. Next, positive photoresist is spread onto the surface the substrate (e.g., by spin coating) and is overlaid with a quartz-chromium mask. The mask is first exposed to Ultra-Violet light and then developed to obtain the image of the multi-electrode-array. Residual unwanted Gold areas are eliminated by reactive ion etching thereby forming the multi-electrode-array leads. The remaining photoresist in removed and an insulator (e.g., Silicon Nitride $Si_3N_4$) is deposited as a continuous layer over the substrate. This may be done, for example, using a plasma enhanced chemical vapor deposition PECVD apparatus, within which Silane and Ammonia form free radicals, which combine on the substrate to form the insulation layer. Next, the electrode tips and the conductive elements are covered with a negative photoresist overlaid by a chromium mask. The insulating layer is then removed from the electrodes by etching to uncover the electrodes. Once the Gold tips are uncovered, each tip is subsequently covered by Titanium Nitride by acceleration within a vacuum tube followed by lift-off technique.

Additional optional and preferred steps of the method include any combination of the following steps: forming a coat or chemically modified surface on the substrate, electrically coupling a coded interface with the conductive elements, providing an external system of amplifiers or forming an internal system of amplifiers on or in the substrate and positioning a pump being in fluid communication with the channels.

Reference is now made to FIG. 10, which is a flowchart diagram of a method of method of positioning at least one cell in at least one addressable position, according to still an additional aspect of the present invention.

The method comprises the following method steps in which in a first step, represented by Block 92, a substrate (e.g., substrate 12) formed with at least one addressable pore and at least one channel is provided, in a second step, represented by Block 94 a liquid medium and the cells is spread over the substrate. In a third step, represented by Block 96 an under-pressure is generated (e.g., by a pump) in the channels so as to adhere the cells onto the pores via vacuum adherence, as further detailed hereinabove. According to a preferred embodiment of the present invention the method comprises an optional step, represented by Block 98, in which electrical signals are sensed of the cells via a plurality of electrode structures.

Reference is now made to FIG. 11, which is a flowchart diagram of a method of a method of measuring electrical activity of a plurality of cells, according to still an additional aspect of the present invention.

The method comprises the following method steps in which in a first step, represented by Block 102, a substrate (e.g., substrate 12) formed with a plurality of addressable pores and a plurality of channels is provided, in a second step, represented by Block 104 a liquid medium and the cells is spread over the substrate. In a third step, represented by Block 106, electrical signals are sensed of the cells via a plurality of multi-electrode-arrays, as further detailed hereinabove. In a fourth step, represented by Block 108 and preferably executed substantially contemporaneously with the third step, fluids are continuously exchanged between a fluid source and the channels and pores. According to a preferred embodiment of the present invention the method comprises an optional step, represented by Block 110, in which an under-pressure is generated (e.g., by a pump) in the channels so as to adhere the cells onto the pores via vacuum adherence, as further detailed hereinabove.

The present invention successfully provides a method of manufacturing an electrode structure. The electrode structure is preferably of nanometric size and can used in many applications, e.g., device 10 and system 40. The method comprising the following method steps which are illustrated in FIGS. 12a-i.

Referring to FIG. 12a, in a first step of the method, substrate 12 is provided. Substrate 12 is preferably semiconductor (e.g., silicon), which may be either a p-type semiconductor or an n-type semiconductor. In a second step of the method a specific region 120 on a first side 122 of substrate 12 is doped by a semiconductor which is different from the semiconductor from which substrate 12 is formed. For example, if substrate 12 is an n-type semiconductor then the doping is preferably with a p-type semiconductor.

FIGS. 12b-c illustrate another step of the method, where FIG. 12b is a bottom view of substrate 12 and FIG. 12c is a side view along a cut, designated A-A' on FIG. 12b. Hence, once substrate 12 is doped with region 120, substrate 12 is passivated, preferably from both sides, so as to protects from environmental effects and to render surfaces 122 and 123 of substrate 12 passive. Many types of passivation procedures may be employed, such as, but not limited to, oxidation, chemical vapor deposition, physical vapor deposition, spattering and the like. The passivation process results in passive layers 124 and 126 on first 122 and second 123 side of substrate 12, respectively. Subsequently, a portion of passive layer 124 is selectively etched in a manner that region 120 is isolated from passive layer 124. In addition, the etching is done so as to at least partially expose region 120. More specifically, recalling that FIG. 12c is a side view along cut A-A', region 120 is not fully covered by portion 125 of layer 124. The exposure of region 120 is better seen in FIG. 12i, below.

FIGS. 12d-e illustrate additional steps of the method, where FIG. 12d is a bottom view of substrate 12 and FIG. 12e is a side view along a cut, designated B-B' on FIG. 12b. Hence, according to a preferred embodiment of the present invention an electrically conducting layer 128 is applied on first side 122 of substrate 12, such that layer 128 is in electrical communication with region 120. This step may be executed by any metallization procedure known in the art, such as, but not limited to, sputtering, evaporation or plating. Layer 128 is preferably made of molybdenum, but other conductive materials are not excluded. Once layer 128 is applied, the method preferably further comprises an additional passivation step, again, to protect from environmental effects and to render the surface of layer 128 passive. The additional passivation process is selected according to the type of metallization (e.g., chemical/physical vapor deposition etc.), and results in an additional passive layer 130.

FIG. 12f is a side view along a cut designated B-B' on FIG. 12b, illustrating an additional step of the method. Hence, according to a preferred embodiment of the present invention substrate 12 is selectively etched from both sides of region 120 and layer 128. The etching procedure of this step is preferably selected so that the echant does not react with layer 130 so that layers 128 and region 120 are protected. For example, for an n-type silicon, an ethylenediamine-pyrocatechol-water (EDP) etch can be used.

Referring to FIG. 12g, the method may further comprise an additional step in which passive layer 126 is etched, for example, by a Buffer Oxide Etch (BOE). Hence, as shown in FIG. 12g, region 120 is in electrical communication with layer 128 and is surrounded by walls 132 of substrate 12. Thus, only electrode structures which are grown on region 120, are isolated from substrate 12, and maintain electrical communication with layer 128.

FIGS. 12h-i illustrate an additional step of the method in which electrode structures 22 are grown (e.g., by chemical vapor deposition) on region 120. The electrical coupling between electrodes 22 and layer 128 are better seen in FIG. 12i, which is a short side view of FIG. 12h.

A particular advantage of the presently preferred embodiment of the invention is that electrode structures 22 are protected by the side-walls, so that further processing such as passivation or cleaning, is allowed, without damaging electrode structures 22.

An isometric view of several electrode structures 22 is shown in FIG. 13. As shown, each electrode is electrically isolated from substrate 12 and is electrically connected to the back-side of substrate 12 via region 120. This embodiment of the preset invention is particularly useful when cells 18 are positioned on device 10 by flow of cells. When a flow is generated in the direction from second side 123 to first side 122 of substrate 12, a portion of the cells is mounted on and adhered to electrode structures 22.

Typical dimensions of the components employed by the present invention are provided hereinbelow.

Hence, in the embodiments in which electrode structures 22 are intracellular electrodes, electrode structures 22 are preferably characterized by an inner diameter of about 5 nm to about 20 nm, an outer diameter of about 50 nm to about 200 nm and a height of about 100 nm to 5000 nm. In these embodiments, the average separation between two electrode structures is from about 50 nm to 300 nm.

In the embodiments in which electrode structures 22 are extracellular electrodes, electrode structures 22 are characterized by an outer diameter of about 10 micrometers to 30 micrometers. In these embodiments, the average separation between two electrode structures is from about 50 micrometers to 300 micrometers.

Channels 16 are preferably characterized by an inner diameter of about 10 micrometers to 50 micrometers, hence channels 16 are preferably microchannels. The length of channels 16 varies with the size of the device employing channels 16

(e.g., device 10). Typically, the length of such devices is in centimeters scale, hence the length of channels 16 is from about a few tenths of centimeters to about a few centimeters.

It is expected that during the life of this patent many relevant nano- and micro-fabrication technologies will be developed and the scope of the terms electrode structures, multi-electrode-arrays and channels are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for positioning at least one cell in at least one addressable position, the device comprising a non-conductive substrate formed with:
    at least one addressable pore;
    at least one channel embedded in said substrate and being in fluid communication with said at least one pore; and
    at least one electrode structure emerging from a base of said at least one pore and being flush with a surface of said substrate;
    said at least one pore and said at least one channel being designed and constructed such that an under-pressure formed in said at least one channel results in vacuum adherence of the at least one cell onto said at least one pore, such that a single cell is vacuum adhered onto a single pore.

2. The device of claim 1, further comprising a plurality of addressable pores and a plurality of channels and being suitable for positioning a plurality of cells in a plurality of addressable positions.

3. The device of claim 2, wherein said substrate is formed with a plurality of electrode structures, each being positioned in one of said plurality of addressable pores.

4. The device of claim 3, wherein at least one of said electrode structures is emerging from a base of said at least one pore and protrudes from a surface of said substrate.

5. The device of claim 3, wherein at least one of said electrode structures is designed and constructed to penetrate into a cell adhered thereto.

6. The device of claim 3, wherein at least one of said electrode structures is designed and constructed to externally engage a cell adhered thereto.

7. The device of claim 2, wherein said plurality of channels and said plurality of addressable pores are designed and constructed so as to allow administration therethrough of different substances to different cells of said plurality of cells.

8. The device of claim 1, wherein said at least one channel and said at least one pore are designed and constructed so as to allow administration therethrough of at least one substance to the at least one cell.

9. The device of claim 1, wherein said substrate is further formed with at least one conductive element embedded therein and electrically coupled to said at least one electrode structure.

10. The device of claim 1, wherein a voltage sensitivity of said at least one electrode is selected so as to allow sensing intracellular potentials.

11. The device of claim 1, wherein a voltage sensitivity of said at least one electrode is selected so as to allow sensing extracellular potentials.

12. The device of claim 1, wherein a voltage sensitivity of said at least one electrode is selected so as to allow transmitting stimuli to the at least one cell.

13. A system for measuring electrical activity of a plurality of cells, the system comprising:
    (a) a non-conductive substrate formed with a plurality of addressable pores and a plurality of channels embedded in said substrate and being in fluid communication with said plurality of addressable pores;
    (b) a plurality of multi-electrode-arrays, each one of said plurality of multi-electrode-arrays includes a plurality of electrode structures formed on a first side of said non-conductive substrate and positioned in one of said pores, such that at least one of said electrode structures emerges from a base of said pore and being flush with a surface of said first side;
    (c) a plurality of conductive elements formed on a second side of said non-conductive substrate, wherein each one of said conductive elements is electrically coupled to one of said electrode structures; and
    (d) a fluid source being in fluid communication with said plurality of channels;
    said pores, said channels, said electrode structures and said fluid source are designed and constructed so that said electrode structures sense electrical signals from the plurality of cells while said fluid source continuously exchanges fluids with said channels and pores.

14. The system of claim 13, wherein said pores and said channels are designed and constructed such that an under-pressure formed in said channels results in vacuum adherence of the plurality of cells onto said plurality of addressable pores, such that a single cell of the plurality of cells is adhered onto a single pore of said plurality of addressable pores.

15. The system of claim 13, further comprising a system of amplifiers being electrically coupled with said plurality of conductive elements.

16. The system of claim 15, wherein said system of amplifiers are integrally formed on or in said non-conductive substrate.

17. The system of claim 13, further comprising a stimulator for generating temporal stimulating electrical signals, transmitted via said electrode structures to the cells at predetermined intervals and in predetermined durations.

18. A method of positioning at least one cell in at least one addressable position, the method comprising:
    providing a substrate formed with at least one addressable pore and at least one channel embedded is said substrate and being in fluid communication with said at least one pore and at least one electrode structure emerging from a base of said at least one pore and being flush with a surface of said substrate;
    spreading a liquid medium and said at least one cell over said substrate; and generating an under-pressure in said at least one channel so as to adhere the at least one cell onto said at least one pore via vacuum adherence, such that a single cell is vacuum adhered onto a single pore, thereby positioning the at least one cell in the at least one addressable position.

19. The method of claim 18, wherein the at least one cell is electrically excitable.

20. The method of claim 18, wherein the at least one cell is selected from the group consisting of a neuron cell, a heart cell, a muscle cell and a pancreatic cell.

21. The method of claim 18, further comprising sensing electrical signals of the at least one cell via at least one electrode structure.

22. The method of claim 21, wherein said sensing is by penetrating the cells, using said at least one electrode structure.

23. The method of claim 21, wherein said sensing is by externally engaging the cells using said at least one electrode structure.

24. The method of claim 18, further comprising administrating at least one substance to said at least one cell via said at least one channel and said at least one addressable pore.

25. The method of claim 18, further comprising continuously exchanging fluids between a fluid source and said at least one channel and at least one pore.

* * * * *